United States Patent [19]

Tilly et al.

[11] 4,005,188

[45] Jan. 25, 1977

[54] X-RAY CONTRAST MEDIA

[75] Inventors: Guy Tilly; Michel Jean Charles Hardouin; Jean Lautrou, all of Aulnay-sous-Bois, France

[73] Assignee: Laboratoires Andre Guerbet, Aulnay-sous-Bois, France

[22] Filed: May 20, 1975

[21] Appl. No.: 579,280

[30] Foreign Application Priority Data

May 31, 1974 United Kingdom ............ 24169/74

[52] U.S. Cl. .............................. 424/5; 260/518 A; 260/501.17; 260/471 A
[51] Int. Cl.² ................. A61K 29/02; C07C 65/20; C07C 65/22
[58] Field of Search ..... 260/518 A, 501.11, 471 A, 260/501.17, 211 R; 424/5

[56] References Cited

UNITED STATES PATENTS

| 2,680,133 | 1/1954 | Wallingford | 260/518 A |
| 3,541,141 | 11/1970 | Bernstein et al. | 260/518 A |
| 3,660,469 | 5/1972 | Bernstein et al. | 260/518 A |
| 3,853,866 | 12/1974 | Obendorf et al. | 260/518 A |

OTHER PUBLICATIONS

Hickinbottom, Reactions of Organic Compounds, pp. 408–412, (1957).

Primary Examiner—James O. Thomas, Jr.
Assistant Examiner—James H. Reamer
Attorney, Agent, or Firm—Young & Thompson

[57] ABSTRACT

This invention relates to compounds of the formula:

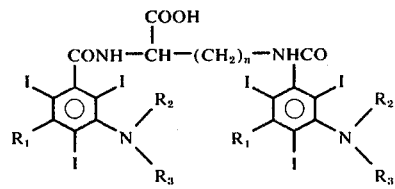

in which:

$R_1$ represents a hydrogen atom or a radical of the formula

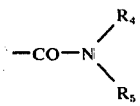

in which $R_4$ and $R_5$ represent, independently of each other, a hydrogen atom or a lower alkyl radical, $R_2$ represents a hydrogen atom or a lower alkanoyl radical, $R_3$ represents a hydrogen atom, a lower alkyl radical or a lower alkanoyl radical, $n$ is 3 or 4, and their lower alkyl esters and their salts with pharmaceutically acceptable bases.

Said compounds are useful as X-ray contrast media.

5 Claims, No Drawings

X-RAY CONTRAST MEDIA

This invention relates to new polyiodo ionic benzene derivatives useful as X-ray contrast media.

The present invention relates, more particularly, to new compounds comprising two benzene nuclei and a single carboxyl group which have low toxicity, provide good contrast, which may be prepared according to industrially useful methods and which, therefore, are of relatively low cost.

The formula of a compound comprising two tri-iodo benzene nuclei and a single carboxyl group has already been given in U.S. Pat. No. 2,708,678. This formula is as follows:

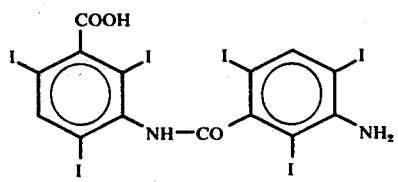

However, the attempts made by Applicant to prepare this compound according to the process described in said patent were all unsuccessful, whatever the operating conditions used.

The present invention relates to compounds of the formula I

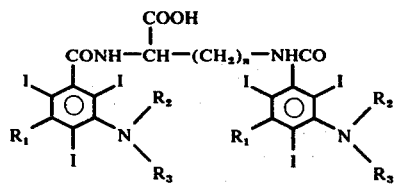

in which:

$R_1$ represents a hydrogen atom or a radical of the formula

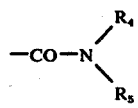

in which $R_4$ and $R_5$ represent, independently of each other, a hydrogen atom or a lower alkyl radical;

$R_2$ represents a hydrogen atom or a lower alkanoyl radical;

$R_3$ represents a hydrogen atom, a lower alkyl radical or a lower alkanoyl radical; n is 3 or 4, and their lower alkyl esters and their salts with pharmaceutically acceptable bases.

By lower alkyl radicals are essentially meant radicals having 1–4 carbon atoms and by lower alkanoyl radicals are essentially meant radicals having 2–6 carbon atoms.

As salts of acids of the formula I may be mentioned, in particular, alkali metal (such as sodium and potassium) salts, the ammonium salts, the alkaline-earth (such as calcium) salts and the organic base salts (e.g. the ethanolamine or methylglucamine salts).

The compounds of the formula I may be prepared by reacting an acid chloride of the formula

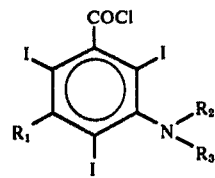

in which $R_1$, $R_2$ and $R_3$ have the meanings given for formula I, with a diamine of the formula:

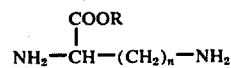

in which R represents a lower alkyl radical and n is 3 or 4.

This reaction may optionally be followed by a saponification, to give an acid of the formula I.

The reaction of acid chloride II with diamine III is advantageously carried out within a polar solvent such as dimethylformamide or dimethylacetamide, in the presence of an acid binding agent such as triethylamine or sodium carbonate, at a temperature of 40°–80° C. The acid chloride is used in an amount of about 2 moles per mole diamine. Reaction time may vary from about 3 hours to about 2 days.

To obtain a compound of the formula I in which $R_2$ and/or $R_3$ are lower alkanoyl radicals, a compound of the formula I in which $R_2$ and $R_3$ are hydrogen atoms may be reacted with an acylating agent, according to conventional methods.

In addition, to obtain a compound of the formula I in which $R_2$ is a lower alkanoyl radical and $R_3$ is a lower alkyl radical, a compound of the formula I in which $R_2$ is a lower alkanoyl radical and $R_3$ is a hydrogen atom may be reacted with a N-alkylating agent, according to conventional methods.

A number of acid chlorides of the formula II are known. The others may be prepared by reacting thionyl chloride with the corresponding acid.

The following examples illustrate the present invention.

EXAMPLE 1

Preparation of N,N'-bis-(2,4,6-triiodo-3-N-methylcarbamyl-5-N-methylacetamido-benzoyl)lysine a. Preparation of 2,4,6-triiodo-3-N-methylcarbamyl-5-N-acetyl-N-methylamino-benzoic acid chloride 2,4,6-Triiodo-3-methylcarbamyl-5-N-acetyl-N-methylamino-benzoic acid (50 g) [described in French Patent 2,085,636] is suspended in thionyl chloride (90 ml). The resulting suspension is heated at 65° C during five hours, with stirring, to give a slurry which is allowed to cool. After suction-filtering and washing the acid chloride with diisopropyl ether, the product is dried in vacuo, to give 37 g of material (i.e., a yield of 73%).

Purity control

Thin layer chromatography (TLC) over Silicagel plate (Merck F 254 grade), after reaction with excess propylamine in dimethylacetamide, eluent: benzene/methylethylketone/formic acid (60:25:20) :

Rf starting acid : 0.5

Rf the condensate with propylamine: 0.85 b. Preparation of N,N'-bis-(2,4,6-triiodo-3-N-methylcarbamyl-5-N-acetyl-N-methylamino-benzoyl)lysine ethyl ester To a suspension of lysine ethyl ester dihydrochloride (17.3 g; 0.07 mole) in a mixture of DMAC (120 ml) and triethylamine (60 g; 0.595 mole) is added, over about fifteen minutes, the acid chloride (100 g; 0.155 mole) dissolved in DMAC (230 ml).

The temperature rises to 25° C. The reaction mixture is then stirred during 1 hour at 50° C and then overnight at room temperature.

Chromatographic control over Silicagel plate in benzene/methylethylketone/formic acid (60:25:20) eluent shows that 5% of the starting acid chloride still remain (Rf = 0.42), and that about 2% to about 3% impurities (Rf = 0.1) have formed together with a product: Rf 0.35, 0.40.

The resulting triethylamine hydrochloride is suction-filtered and washed with the minimum amount of DMAC. The reaction liquors are poured over ice-water(800 ml). The resulting material is stirred several hours at room temperature, after which it is suction-filtered, washed with water and dried, to give 48.5 g of material.

A second crop is obtained by adding water (200 ml) to the filtrate: 6 g.

Chromatographic control shows both crops are identical. Overall yield: 70%.

c. Saponification 54 g of ester are suspended in 2N sodium hydroxide (155 ml). Dissolution does not occur but, after 2 hours, the product turns to a gum: the latter is taken up into water (120 ml), upon which solubilization occurs. TLC shows the absence of ester. The material is neutralized with hydrochloric acid to pH 7. It is then charcoaled at 60° C. during one hour, filtered and adjusted to pH 3 with hydrochloric acid. It is then suction-filtered, washed repeatedly with water and drid overnight at 60° C, to give 42 g of creamy-white product (Yield: 79%).

d. Purification 45 g of acid are dissolved in 1N sodium hydroxide (33 ml). Water (90 ml) is added thereto. pH value is 8. The solution is adjusted to pH 7 with acetic acid, and is then treated with 35A grade charcoal at 60° C during 1 hour. This treatment is repeated twice, but at pH 6. The material is precipitated with dilute (1/10) hydrochloric acid at room temperature, after which it is suction-filtered, washed with water and dried, to give 33.5 g of white product (Yield: 74%).

Purity control

Iodine titration: 100.5%
acidity determination with sodium methoxide: 98.5%
TLC over Silicagel plate, benzene/methylethylketone/formic acid eluent (60:25:20): Rf = 0.3;
ethyl acetate/isopropanol/ammonia eluent (55:35:20): separation into two isomers: Rf = 0.3 and 0.33.

EXAMPLE 2

Preparation of
N,N'-bis-(2,4,6-triiodo-3-N-methylcarbamyl-5-acetamido-benzoyl)lysine a. Preparation of 2,4,6-triiodo-3-N-methylcarbamyl-5-amino-benzoic acid chloride The procedure described in Example 1a is used, with 2,4,6-triiodo-3-N-methylcarbamyl-5-aminobenzoicacid as starting material (Yield: 85%). TLC after condensation with ethanolamine, in benzene/methylethyl ketone/formic acid eluent (60:25:20):
Rf of starting acid 0.8
Rf of condensate with ethanolamine 0.4 b. Condensation of lysine ethyl ester with 2,4,6-triiodo-3-N-methylcarbamyl-5-aminobenzoic acid chloride The procedure described in Example 1b is used: gross yield: 66%.
TLC in chloroform/acetone/acetic acid (40:50:10) eluent:
Rf of starting acid :0.3
Rf of acid chloride :0.95
Rf of condensate :0.85
Iodine titration : 98.5% c. Saponification

The precedure described in Example 1c is used: gross yield: 80%.
TLC in chloroform/acetone/acetic acid (40:50:10) eluent:
Rf of starting ester : 0.85
Rf of resulting acid : 0.45
Titration with sodium methoxide : 123%.

d. Acetylation-purification

It is conducted according to conventional methods, in dimethyl formamide solution, with acetyl chloride, during 16 hours, with stirring, at room temperature.

After precipitation with ether followed by crystallization from water, the product is suction filtered, washed and dried. Yield : 68%.
TLC in acetone/chloroform/acetic acid (50:40:10) eluent:
Rf of unacetylated product: 0.45
Rf of acetylated product : 0.4
In benzene/methylethylketone/formic acid (20:25:60) eluent:
Rf of unacetylated product: 0.4
Rf of acetylated product : 0.2
Titration with sodium methoxide : 99%
Iodine titration : 98.5%

EXAMPLE 3

Preparation of
N,N'-bis-(2,4,6-triiodo-3-N-methylacetamido-benzoyl)lysine a. Preparation of 2,4,6-triiodo-3-N-methylacetamido-benzoic acid chloride.

The procedure described in Example 1a is used, with 2,4,6-triiodo-3-N-methylacetamido-benzoic acid as starting material (Yield: 85%).

b. Condensation of lysine ethyl ester with 2,4,6-triiodo-3-N-methylacetamido-benzoic acid chloride.

The procedure described in Example 1b is used. Gross yield is 81%.
TLC: benzene/dioxane/acetic acid (45:50:20) eluent:
Rf of starting acid : 0.05
Rf of condensate : 0.3 c. Saponification.

The procedure described in Example 1c is used. Gross yield is 90%.
TLC : benzene/methylethylketone/formic acid (40:10:5) eluent:
Rf of ester: 0.45
Rf of acid product : 0.15 d. Purification

Purification is carried out by precipitation, in acid medium, of an alkaline solution, with repeated charcoal treatments at neutral pH. Yield: 27%.

TLC : benzene/methylethylketone/formic acid (40:10:5) eluent:
Rf = 0.4
benzene/dioxane/acetic acid eluent (45/50/20)
Rf : 0.0
Titration with sodium methoxide : 102%
Titration with tetrabutylammonium hydroxide : 98.5%
Iodine titration : 99%

PREPARATION OF PHARMACEUTICAL SOLUTIONS

Pharmaceutical solutions said to contain 28% and 36% iodine (i.e., containing 28 g and 36 g iodine per 100 ml) could be obtained using the compounds as the methylglucamine salt:
pH prior to sterilization : 7.2
pH after sterilization : 7.1.
Results of osmolality determinations are given in the following Table.

OSMOLALITY DETERMINATION

Osmolality is determined by extrapolation of the values obtained on successive dilutions of methylglucamine salt solutions containing 28% iodine.

Osmolality readings are made using a Model 230/D/330 D FISKE osmometer. This apparatus indicates this determination as milliosmoles per kg of solution. Its operation is based on the principles of cryoscopy.

In the following Table:
a = 2,4,6-Triiodo-3-N-methylcarbamyl-5-acetamido-benzoic acid (iothalamic acid)
b = 2,4,6-Triiodo-3-N-hydroxyethylcarbamyl-5-acetamido-benzoic acid (ioxithalamic acid)
c = 5,5'-Adipoyldiimido-bis(2 4,6-triiodo-N-methylisophthalamic acid) (iocarmic acid).

| Compound | Osmolality (mosm/kg) |
| --- | --- |
| Example 1 | 475 |
| a | 1410 |
| b | 1390 |
| c | 950 |

It is apparent that, as the methylglucamine salt, the compounds of the formula I possess an osmolality markedly lower than that of the reference materials.

The results of a toxicological and pharmacological investigation of the compounds of the formula I are given below.

1. DL$_{50}$ in mice, by the intravenous route

Solutions containing 28% iodine were injected intravenously in mice (weighing 20 ± 2 g), at a rate of 2 ml/minute. For comparative purposes, the LD$_{50}$ values obtained under the same conditions with currently used solutions are also indicated in the following Table:

| Compound (as the methylglucamine salt) | LD$_{50}$ |
| --- | --- |
| Example 1 | 9.5 |
| ioxithalamate | 5.6 |
| iocarmate | 6.2 |
| iothalamate | 5.4 |

2. Investigation of the clearance in cats of the compound of Example 1.

0.10 g iodine/kg is administered intravenously. No reaction on completion of the injection.

The bladder becomes opaque within the first fifteen minutes after injection.

The gall bladder is faintly visible 1.5 hour later. The opacity increases gradually to reach a maximum 4 hours after injection.

Thus, clearance occurs via the hepatic and renal routes.

It is apparent from the above data that the compounds of the formula I are useful X-ray contrast media. The chief applications of said compounds are urography and cholangiography.

The preferred pharmaceutical form of the contrast media consists of the aqueous solutions of salts of the compounds of the formula I.

The aqueous solutions contain advantageously 50–100 g of salt per 100 ml and the injectable amount of such solutions may vary within the range from about 5 ml to about 500 ml.

Having now described our invention what We claim as new and desire to secure by Letters Patent is:

1. Compounds of the formula :

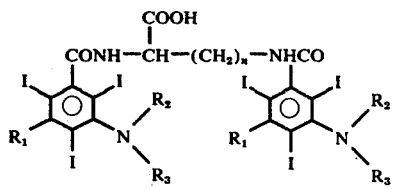

in which:
R$_1$ is selected from the group consisting of hydrogen and a radical of the formula

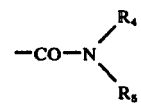

in which R$_4$ and R$_5$, independently of each other, are selected from the group consisting of hydrogen and a lower alkyl radical,
R$_2$ is selected from the group consisting of hydrogen and a lower alkanoyl radical,
R$_3$ is selected from the group consisting of hydrogen, a lower alkyl radical and a lower alkanoyl radical,
n is 3 or 4,
and their lower alkyl esters and their salts with pharmaceutically acceptable bases.

2. N,N'-bis-(2,4,6-triiodo-3-N-methylcarbamyl-5-N-methyl-acetamido-benzoyl)lysine and its salts with pharmaceutically acceptable bases.

3. N,N'-bis-(2,4,6-triiodo-3-N-methylcarbamyl-5-acetamido-benzoyl)lysine and its salts with pharmaceutically acceptable bases.

4. N,N'-bis-(2,4,6-triiodo-3-N-methylacetamido-benzoyl)-lysine and its salts with pharmaceutically acceptable bases.

5. An X-ray contrast medium consisting essentially of a compound as claimed in claim 1, in a pharmaceutically acceptable carrier.

* * * * *